United States Patent [19]

Ootani et al.

[11] Patent Number: 4,820,825

[45] Date of Patent: Apr. 11, 1989

[54] METHOD FOR PURIFYING TRYPTOPHAN

[75] Inventors: Masaru Ootani; Masami Kojima; Toshio Kitahara, all of Kawasaki, Japan

[73] Assignee: Ajinomoto Co., Inc., Tokyo, Japan

[21] Appl. No.: 143,847

[22] Filed: Jan. 14, 1988

[30] Foreign Application Priority Data

Jan. 14, 1987 [JP] Japan .................................. 62-7003

[51] Int. Cl.$^4$ .......................................... C07D 209/20
[52] U.S. Cl. .................................................. 548/496
[58] Field of Search ........................................ 548/496

[56] References Cited

U.S. PATENT DOCUMENTS

| | | | |
|---|---|---|---|
| 2,416,956 | 3/1947 | Sahyun | 548/497 |
| 3,450,712 | 6/1969 | Samejima | 548/497 |
| 3,801,457 | 4/1974 | Arima et al. | 195/29 |

FOREIGN PATENT DOCUMENTS

| | | |
|---|---|---|
| 0200944 | 11/1986 | European Pat. Off. . |
| 1545685 | 8/1969 | Fed. Rep. of Germany . |
| 659828 | 2/1987 | Switzerland . |
| 1189796 | 4/1970 | United Kingdom . |
| 1222904 | 2/1971 | United Kingdom . |

*Primary Examiner*—David B. Springer
*Attorney, Agent, or Firm*—Oblon, Fisher, Spivak, McClelland & Maier

[57] ABSTRACT

A process for purifying tryptophan produced by microbial cells or an enzyme is disclosed. In this process, the microbial cells are separated, the solution containing tryptophan is treated at a pH in the range of 1 to 4 with activated carbon and a non-polar highly porous resin and crystallized under neutralization in the presence of a lower aliphatic alcohol or a lower aliphatic ketone.

The thus purified tryptophan has a transmission of 95% and more.

8 Claims, No Drawings

METHOD FOR PURIFYING TRYPTOPHAN

BACKGROUND OF THE INVENTION

1. Field of the Invention

The present invention relates to methods for purifying tryptophan (Trp) which comprise removing impurities, such as proteins and colored substances, from Trp obtained from a Trp-containing solution.

2. Discussion of the Background

Trp is one of the essential amino acids. It is useful as a food additive, as an additive to animal feed, in medicine or for producing health foods.

In processes for producing Trp by fermentation using bacterial cells, glucose is employed as a main starting material. The crude crystals of Trp which are produced by this method however contain impurities such as proteins and colored materials.

It is very difficult to remove these impurities, from the Trp product irrespective of their quantity, since they have high hydrophobicity. Conventional recrystallization for example does not result in a good purification of Trp, since such impurities are incorporated in the surface of the Trp crystals or between the crystals. Therefore tryptophan obtained by such process does not fulfill the standard requirements for products which are to be employed, e.g., for medical supplies, which must have high purity (characterized by a transmission of 95% or more at $\lambda = 430$ nm).

Hence it has become necessary to develop a purification method by which highly purified non-colored Trp with a transmission of 95% or more is obtainable from a Trp-containing reaction solution.

In a known method (Japanese laid open patent application No. 895/1983) crude tryptophan is purified by treating an aqueous solution containing crude tryptophan with a non-polar, highly porous resin and by subsequent filtration with an ultrafiltration membrane to remove the reaction impurities which have accumulated in the solution. It has been found that impurities having a molecular weight of 500 to 5000 are responsible for the decrease of the transmission value. The method using an ultrafiltration membrane (i.e. according to Japanese laid open patent application No. 895/1983) cannot remove such impurities.

According to another known method (Japanese laid open patent application No. 39857/1984) the solution containing crude Trp is adjusted to an alkaline pH value and is crystallized by neutralization in the presence of a lower aliphatic alcohol or a ketone. In this process the degree of removal of impurities is insufficient and it is difficult to obtain crystals having a transmission value of 95% or more.

According to a further process (Japanese laid open patent application No. 126070/1986), a solution of Trp obtained by an enzymatic reaction, is heated to a temperature of 95° to 100° C. at an acidic pH in the presence of activated carbon. The solution is separated from the solid material by filtration. The filtrate containing Trp is contacted with a non-polar highly porous resin and concentrated. After this operation, a lower aliphatic alcohol is added to the solution. In this method, however, decomposition and formation of colored material are caused when the reaction solution produced by fermentation and containing particularly large amounts of impurities is heated to a temperature of 95° to 100° C. in the presence of activated carbon. This is due to the instability of the indole ring of tryptophan.

There is therefore a need for a process for obtaining purified tryptophan from an aqueous solution containing this material, where the process provides a high quality product and does not suffer from the disadvantages discussed above.

SUMMARY OF THE INVENTION

Accordingly, it is an object of this invention to provide a process for purifying tryptophan.

It is another object of this invention to provide a process for purifying a tryptophan product contaminated with proteins.

It is another object of this invention to provide a process for purifying a tryptophan product contaminated with colored materials.

It is another object of this invention to provide a process which provides for a high degree of removal of impurities from a tryptophan product.

It is another object of this invention to provide a process for obtaining high purity tryptophan from an aqueous solution containing tryptophan and impurities.

It is another object of this invention to provide a process for obtaining high purity tryptophan from an aqueous solution containing tryptophan where the tryptophan is produced by bacterial cells.

It is another object of this invention to provide a process for obtaining high purity tryptophan from an aqueous solution containing tryptophan where the tryptophan is produced enzymatically.

The inventors have now discovered a process which satisfies all of these objects and other objects which will become apparent from a reading of the description given hereinbelow. In this process for purifying tryptophan, an aqueous solution containing crude tryptophan is treated at a pH in a range of from 1 to 4 with activated carbon and with a non-polar highly porous resin. The treated solution is then neutralized with an alkaline substance, and tryptophan is crystallized from the solution in the presence of a lower aliphatic alcohol or a lower aliphatic ketone. This process provides a high quality tryptophan product.

DETAILED DESCRIPTION OF THE PREFERRED EMBODIMENTS

The present inventors have intensively studied the above-mentioned problems with existing systems and found that proteins and colored material impurities may be removed, and that further the durability of the resin is improved by treating aqueous solutions of Trp at an acidic pH-value of 1 to 4.

The present invention therefore relates to a process for purifying tryptophan. This process comprises treating an aqueous solution containing crude tryptophan (i.e. the solution contains tryptophan and impurities) at a pH in the range of 1 to 4 with activated carbon and with a non-polar highly porous resin. The treated solution is then neutralized with an alkaline substance and tryptophan is crystallized from the solution through the addition of a lower aliphatic alcohol or a lower aliphatic ketone.

The process of the present invention provides crystals of Trp having the desired transmission of 95% or more.

The starting solution of Trp, which is purified according to the present invention, may be an aqueous solution obtained by dissolving crude Trp. Preferably it may be a solution obtained from a fermentation in which bacterial cells or enzymes are used. If bacterial cells have been used, these are removed from the solution before the process of the invention is carried out. The microbial cells are removed using known methods, for example with an ultrafiltration membrane.

The concentration of the acidic starting solution of crude Trp is not particularly limited. However, a Trp concentration of 5 to 20 g dl$^{-1}$ is preferable in view of reducing the concentration for the treatment with the resin.

The amount of activated carbon, which is added to the acidic Trp solution, is varied in accordance with the quantity of impurities in the crude crystals or the crude solution of Trp. It is, however, generally in the range of about 3 to 25% by weight of activated carbon, based on the amount of Trp.

The activated carbon is preferably washed with a diluted acid, for example diluted hydrochloric acid, before it is added to the solution.

The treatment with the activated carbon is preferably conducted at a temperature of 50° C. or less, since Trp decomposes at higher temperatures with the formation of a colored substance. A tie period of 15 to 30 minutes is sufficient for the treatment.

In the subsequent process step the solution is treated with a non-polar, highly porous resin.

The non-polar, highly porous resin used in the present invention comprises a styrene-divinyl benzene polymer as the main structure or a halogenated derivative of such polymer. This resin has a high specific gravity. Useful resins are for example resins of the Diaion HP series and SP series (Mitsubishi Kasei Industries Co.), XAD-4 (Roehm & Haas Co.), 0C1031 (Bayer) and similar resins. The resins are however not limited to the above-stated examples. Also other nonpolar, highly porous resins may be used for the purpose of the invention, as far as they have the same properties which are the same or similar to those of the above-defined resins.

The resins SP 206 and 207, which have a particularly high specific gravity, are suitable when the quantity of impurities to be adsorbed is high. The resin which has adsorbed the impurities may be reactivated for example by treatment with an alkaline aqueous solution, an organic solvent, such as a lower aliphatic alcohol, acetone and a lower aliphatic ether or an aqueous mixture of such solvent. The term "lower aliphatic" in this document refers to aliphatic groups having from 1 to 6 carbon atoms and water miscible solvent unless otherwise noted.

The contact between the resin and the solution may be achieved by two methods. Either a batchwise method or a continuous method using a column may be used. The column method is preferred, since it is more convenient.

The space velocity of the flow of the solution through the column is not particularly limited. A value of about 0.5 to 10 h$^{-1}$ (SV) is usual.

The column is held at a temperature which depends on the thermal resistance of the resin used. A temperature of 50° C. or less is preferable in order to prevent the decomposition of Trp.

The quantity of resin used is varied depending on the quantity of the proteins and the colored materials left in the solution after treatment with activated carbon. A smaller quantity of the resin is preferable in order to decrease product loss due to adsorption of Trp into the resin (60 to 80 g l$^{-1}$ of the resin). Trp adsorbed to the resin may be eluted with water. If, therefore, the resin is washed with about 5 parts by volume of water, loss of Trp due to adsorption may be limited to less than several percents.

The quantity of Trp treated with a specific resin varies within a broad range depending on the impurities contained in the crude Trp crystals used as the starting material. Several hundred grams to several kilograms Trp per liter of resin may be treated.

To the treated acidic solution obtained an alkaline substance is then added in the presence of a water-miscible lower aliphatic ketone, e.g., a $C_{3-9}$ ketone, in a crystallizing vessel. To get a good recovery it is preferable to use a smaller amount of isopropanol. In order to promote the growth of Trp crystals, the alcohol or ketone, such as isopropanol, is used in such amount that its concentration is 5 to 30% (volume/volume) after neutralization.

The mixture is preferably held at a higher temperature in order to promote the growth of Trp crystals. In view of the decomposition of Trp it is, however, preferred to limit the temperature to 50° C. or less.

The pH value after the completion of the neutralization is not particularly limited, since Trp has almost the same solubility at a pH value of 3 to 8. A pH value of 5 or more is however preferable in view of the fact that the isoelectric point of the impurities (peptdes) is at a pH value of 3 to 4.

Other features of this invention will become apparent in the course of the following descriptions of exemplary embodiments. These exemplary embodiments are given for illustration of the invention. They are not intended to be limiting thereof.

EXAMPLE 1

Production of crude Trp product

A 35% HCl solution was added to L-tryptophan fermentation liquid obtained by culturing variants belonging to the genus Bacillus, the genus Brevibacterium, the genus Corynebacterium, the genus Anthrobacter, etc. until the pH reached 3, then the solution was centrifuged. Ten liters of the bacteria free liquid separated by centrifuging was filtered at 35° C. under a pressure of 2 kg/cm$^2$ using an Asahi Chemical Industry's ACL-1010 ultrafiltration module (fractional molecular weight: 13,000). When about 9 l of the filtrate had been obtained, the remainder was diluted by adding 6 l of water. Filtering was continued until a total of 15.7 l of filtrate was obtained.

A 30% NaOH solution was added to 2 l of the ultrafiltrate thus obtained until the pH reached 12.5. The result was concentrated, then 130 g of the concentrated liquid (tryptophan content: 16.1%) was added to 50 ml of acetic acid.

The resulting solution was neutralized and allowed to crystallize at 45° C. for 2 hours, then cooled to 25° C. The precipitated crystals were centrifuged out then cleaned by spraying with a small amount of water. L-tryptophan crystals were obtained by drying the precipitated and cleaned crystals at 70° C. under reduced pressure.

The tryptophan crystal thus obtained weighed 19.9 g, and had a purity of 99.1%. The yield was 94.2% and crystal transmittance was 90%. (Conditions for measuring transmittance 1.0 g tryptophan crystal +10 ml water, 430 nm wavelength, 10 mm cell length).

Purification of the Trp product

Crude crystals of Trp (transmission =10 %; 24 g) obtained from the Trp fermentation liquor described above were dissolved in water and sulphuric acid to give a solution having a concentration of 8g/dl and a pH value of 1.8.

Activated carbon (4.8 g) which had been washed with diluted hydrochloric acid, was added to the aqueous solution which was then stirred for 15 minutes at 50° C., and filtered through a millipore filter with a pore size of 0.45 μm. The filtrate thus obtained was passed through a column of 4 ml ($\phi \times L = 1$ cm $\times$ 6.4 cm) containing a non-polar highly porous resin ("SP 207", produced by Mitsubishi Kasei Industries Co.) at a space velocity SV of 5. Isopropanol (70 ml) was added to the percolated liquor, and then a 10% aqueous sodium hydroxide solution was slowly added thereto at 50° C. to crystallize Trp by neutralization.

At the end of the neutralization, the solution was cooled to 20° C. at a rate of 5° C./h; after 12 hours, crystals of Trp were obtained on a paper filter and washed with 10% of isopropanol in water (50 ml).

After drying the crystals in air, Trp in crystalline form having a transmission of 95.4% was obtained at a yield of 18 g.

EXAMPLE 2

After filtering the tryptophan fermentation liquid by using Celite as a filtration assistant, the filtrate (tryptophan concentration: 15 g dl$^{-1}$ was concentrated and crystallized at 60° C. under reduced pressure. The obtained slurry was gradually cooled to 40° C. to separate the crystals. The result was a crude crystal (α crystal), which was dissolved in aqueous NaOH solution. The liquid was subjected to various kinds of neutralization-crystallization methods. The tryptophan concentration of the liquid for crystallization was 10 g dl$^{-1}$, and the pH was 12.

A 5-dl aliquot of the liquid was neutralized and crystallized at 60° C. from the alkali side using 36.7 N sulfuric acid. After neutralization to pH 6, the liquid was cooled to a temperature of 30° C. An experiment was conducted under the same conditions as the above except that 20 v/v % of 1-propanol or methanol were added separately to the liquid before neutralization with sulfuric acid. Further, the crude crystal was dissolved in water and 36.7 N sulfuric acid for crystallization (tryptophan concentration: 10 g dl$^{-1}$, pH 1). Neutralization crystallization was done from the acid side, by using NaOH at 60° C. After neutralization to pH 6, it was cooled to a temperature of 30° C.

The crystal in the obtained slurry was separated by a centrifugal dehydrator and cleaned with a small amount of water.

Table 1 shows the properties of the crystals obtained in the experiments.

TABLE 1

|  | General neutralization-crystallization method (control) | Neutralization crystallization from acid side | Addition of 1-propanol | Addition of methanol |
|---|---|---|---|---|
| Crystal form | β crystal | β crystal | α crystal | α crystal |
| Grain size (μ) | 100~150 | 50~100 | 300~350 | 200~250 |
| Nitrogen purity* (%) | 90 | 86 | 98 | 93 |
| Coloring** | 0.45 | 0.65 | 0.06 | 0.09 |

*Tryptophan nitrogen/(all nitrogen-ammonia nitrogen).
** These data were obtained by dividing the value of $-\log T$ at wavelength of 430 nm for the solution in which crude crystal is dissolved by the tryptophan concentration of this solution.
T is the transmittance.

Purification of the Trp product

Crude crystals of Trp having a transmission of 89% (24 g), obtained from the Trp fermentation liquor described above were dissolved in water and sulphuric acid to give a solution having a concentration of 12 g/dl and a pH value of 1.5.

Activated carbon (1.2 g) which had been washed with diluted hydrochloric acid was added to the aqueous solution which was stirred for 15 minutes at 30° C. and then filtered through a millipore filter with a pore size of 0.45 μm. The filtrate obtained was passed through a column of 4 ml ($\phi \times L = 1$ cm $\times$ 6.4 cm) containing a non-polar highly porous resin ("SP 206", produced by Mitsubishi Kasei Industries Co.) at a space velocity SV = 10. isopropanol (35 ml) was added to the percolated liquor, and then an aqueous 10% sodium hydroxide solution was slowly added thereto at 30° C. to crystallize Trp at neutralization.

In the same manner as in Example 1, Trp in the crystalline form having a transmission of 98.2% was obtained at yield of 20 g.

It is clear from the above that in the present invention Trp produced by fermentation or enzymatic reaction can be highly purified. The present invention can be used on a large scale and is therefore industrially very advantageous.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for obtaining purified tryptophan from an aqueous solution containing tryptophan and impurities, said process comprising:
   treating an aqueous solution containing tryptophan and impurities at a pH in the range of from 1 to 4, with activated carbon and a non-polar highly porous resin;
   neutralizing the treated solution with an alkaline substance; and
   crystallizing the tryptophan from said solution in the presence of a $C_{1-6}$ aliphatic alcohol or a $C_{3-9}$ aliphatic ketone.

2. The process of claim 1, wherein a solution containing from 5 to 20 g dl$^{-1}$ trytophan is subjected to the treatment.

3. The process of claim 1, wherein the solution is treated with 3 to 25% by weight of activated carbon, based on the weight of tryptophan.

4. The process of claim 1, wherein the activated carbon used is activated carbon which has been washed with a dilute mineral acid.

5. The process of claim 1, wherein the crystallization is carried out in the presence of isopropanol at a concentration of from 5 to 30% (v/v), based on the volume of solution.

6. The process of claim 1, wherein the crystallization step is carried out by neutralizing the solution to a pH of 5 to 8.

7. The process of claim 1, wherein the aqueous solution containing tryptophan and impurities is an aqueous solution obtained from a fermentation process which uses bacterial cells and from which said bacterial cells have been separated.

8. The process of claim 1, wherein said aqueous solution containing tryptophan and impurities is an aqueous solution obtained from a fermentation process which uses at least one enzyme and from which bacterial cells have been removed.

* * * * *

UNITED STATES PATENT AND TRADEMARK OFFICE
CERTIFICATE OF CORRECTION

PATENT NO. : 4,820,825
DATED : April 11, 1989
INVENTOR(S) : MASARU OOTANI, ET AL.

It is certified that error appears in the above-identified patent and that said Letters Patent is hereby corrected as shown below:

Column 1, line 61, 2 words, "material" and "by".

Column 3, line 24, "tie" should read --time--.

Column 3, line 36, "nonpolar" should be --non-polar--.

Column 4, line 28, "peptdes" should read --peptides--.

Column 5, line 32, "15g dl$^{-1}$" should read --15g dl$^{-1}$)--.

Column 5, line 49, "Neutralization crystallization" should be --Neutralization-crystallization--.

Column 6, line 29, the word "isopropanol" should read --Isopropanol--.

Signed and Sealed this

Third Day of July, 1990

*Attest:*

HARRY F. MANBECK, JR.

*Attesting Officer*  *Commissioner of Patents and Trademarks*